United States Patent [19]

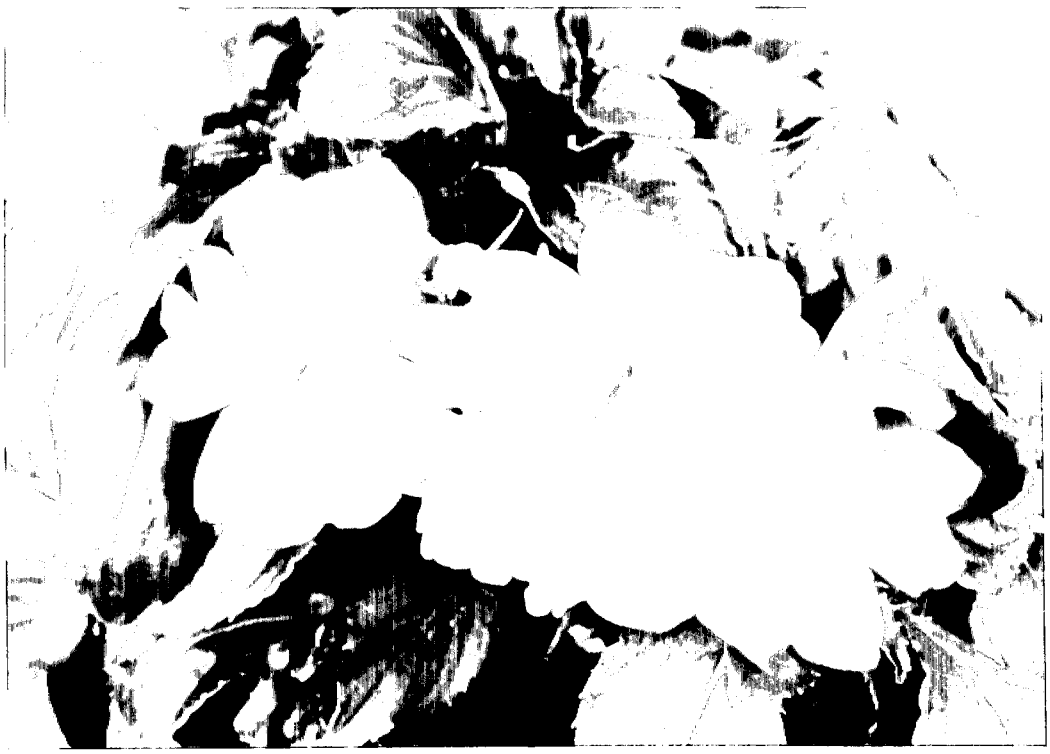

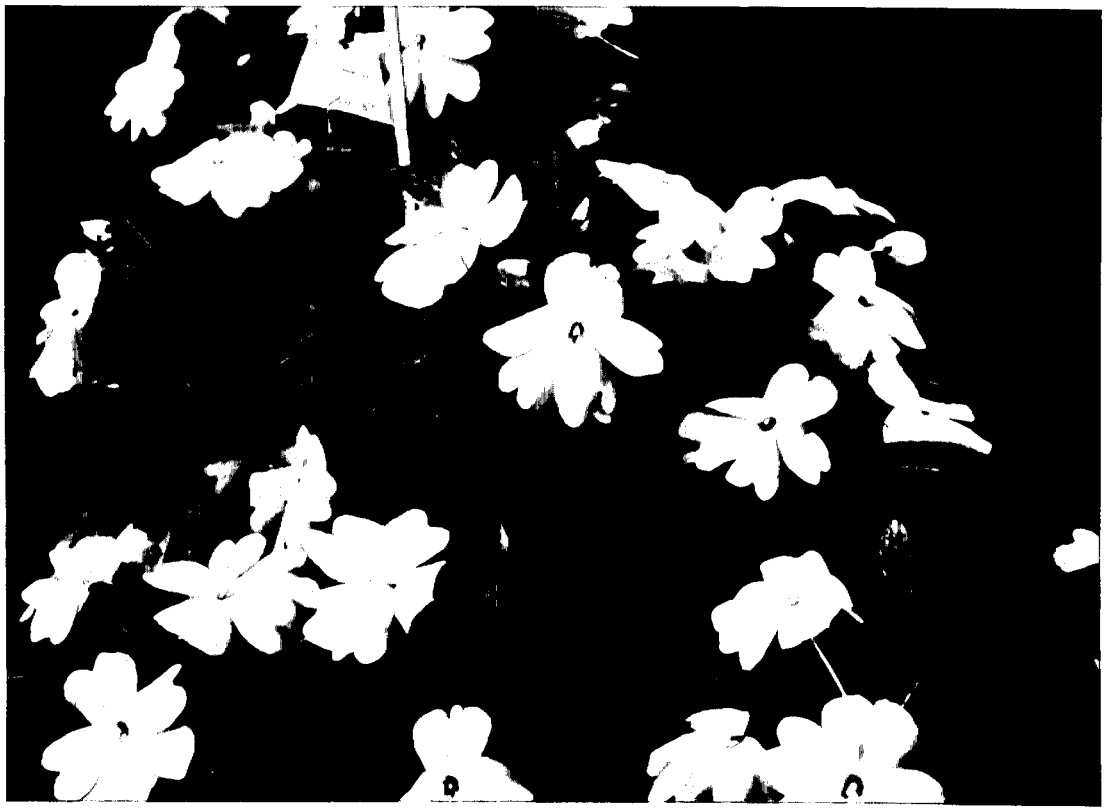

Hope

[11] Patent Number: Plant 5,699

[45] Date of Patent: Mar. 25, 1986

[54] IMPATIENS PLANT NAMED VISTA IMPATIENS NO. 60

[75] Inventor: Claude Hope, Cartago, Costa Rica

[73] Assignee: Pan American Plant Co., Parrish, Fla.

[21] Appl. No.: 566,804

[22] Filed: Dec. 29, 1983

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of impatiens plant known by the cultivar name Vista Impatiens No. 60, characterized by its very large, vivid dark salmon color flowers with the half eye, profuse blooming, dark green foliage, good self-branching habit, good keeping qualities, and tall, upright and spreading form, making the cultivar suitable for bedding plants, hanging baskets and container culture.

2 Drawing Figures

The present invention relates to a new and distinctive cultivar of Impatiens plant, botanically known as Impatiens, and known by the cultivar name Vista Impatiens No. 60.

The new cultivar is the result of a planned program of hybridization, the purpose of which was to obtain a series of plants having a wide range of colors and very large flowers derived from the New Guinea complex of species collected by the Longwood Garden Expedition of 1970. The cultivar comprising the present invention was selected in 1982 and designated seedling No. 3549-2. The new seedling was developed through controlled breeding by crossing seedling No. 3310-11 (the variety Mount Kum P.I. 354255) × 3402-1 (from Impatiens Mooreana P.I. 366030).

Asexual reproduction by terminal or stem cuttings taken by me at Cartago, Costa Rica has shown that the unique features of the new cultivar are stabilized and are reproduced true to type in successive propagations.

The following characteristics distinguish the new impatiens from both its parent varieties and other cultivated impatiens of this type known and used in the floriculture industry:

1. Vista Impatiens No. 60 was selected primarily for its brilliant dark salmon color and its unique lighter colored center which appears as a half eye.
2. The flower size is very large (74 mm.).
3. Plant flowers profusely under optimum conditions (80° F. days and 60° F. nights).
4. Rate of growth is moderate, producing in 6–8 weeks in a 5½" pot a saleable plant 25–30 cm. tall and 40 cm. in diameter when grown under full sun in the fall, winter and spring, and under light shade in the summer in Florida.
5. Habit is tall (45–60 cm. when full grown), and upright and spreading, thereby making the cultivar ideal for bedding plants, container culture and hanging baskets.
6. Foliage is dark green, providing an excellent contrast to flower color.
7. Exhibits good self-branching habits.
8. Exhibits good keeping qualities.

In the accompanying drawings, Sheet 1 comprises a color photograph illustrating the overall appearance of the new cultivar, with the flower color in Sheet 1 being somewhat more pink than the actual flower color. Sheet

2 is an enlarged black and white photograph, with the true flower color being illustrated on one flower.

The following is a detailed description of my new impatiens cultivar based on plants produced under commercial practice in Cortez and Parrish, Fla. The plants were grown outdoors in full sun during fall, winter and spring, and under light shade during the summer months. Color references are made to The Royal Horticultural Society Colour Chart except where general terms of ordinary dictionary significance are used.

Parentage: Seedling No. 3310-11 (from variety Mount Kum P.I. 354255) × 34-2-1 (from Impatiens Mooreana P.I. 366030).

Propagation:

A. *Type cutting.*—Tip cuttings with 5 cm. stems.

B. *Time to initiate roots.*—10–14 (days) at 27° C. summer; 12–16 (days) at 18° C. winter.

C. *Rooting habit.*—Abundant and fibrous.

Plant description:

A. *Form.*—Tall and generally upright (45 cm.–60 cm. when full grown) but somewhat spreading; good self-branching habits.

B. *Habit of growth.*—Rate of growth is moderate for this type of plant. Vegetative shoots are formed at the lower nodes and flowers at the higher nodes.

C. *Foliage description.*—Lower leaves opposite, higher leaves in whorls of 5. Leaves are simple. (1) Size: Average full grown leaf is 130 mm. long×51 mm. wide. Full grown leaves have petioles 25 mm. long. Young leaves have very short (5 mm. long) petioles. (2) Shape: Elliptic; apex slightly acuminate, base attenuate. (3) Texture: Smooth, glabrous. (4) Margin: Serrulate. (5) Color, young foliage, top side close to green 138A, under side close to greyed green 191B; mature foliage, top side green 137A, under side close to greyed green 191B. (6) Venation: Pinnate, main vein close to greyed green 193A.

Flowering description:

A. *Flowering habits.*—Very floriferous, flowers occurring progressively around the whorl of leaves. Flowers are large and single.

B. *Natural flowering season.*—Flowering is indeterminate and occurs throughout the year except for periods of high light and high temperatures in Florida.

C. *Flower buds.*—Conical, covered with 3 sepals. Upper two sepals are 10 mm. long × 7 mm. wide, apex acuminate. Lower sepal is 16 mm. long × 12 mm. wide, apex acuminate. Upper sepals are green in color, the lower sepal is colorless infused with pink at the base and with green at the apex. Apex of lower sepal is green. A hollow spur is connected to the lower sepal, and is 50 mm. long when full grown and colorless but heavily infused with red.

D. *Flowers borne.*—On peduncles 51 mm. long, green in color.

E. *Quantity of flowers.*—One flower per leaf, occurring progressively around the whorl of leaves.

F. *Petals.*—(1) Shape: Top petal heart-shaped with a broad rounded base. Other petals heart-shaped with pointed base. Occasionally petals may have an added lobe in the middle of the two curves that join to form top of heart. (2) Color: Top side 52B, with a salmon-white eye on the lower two petals, the main color fading to 52C-D; underside 52C-D. (3) Number of petals: Five; with the middle and bottom petals being united at the base on each side. (4) Size of flowers: Top petal 33 mm. long × 39 mm. wide; 2 middle petals 39 mm. long × 26 mm. wide; 2 bottom petals 40 mm. long × 30 mm. wide. Total flower diameter is 74 mm.

G. Reproductive organs.—(1) Stamens: Five; with the lower stamen being shorter than the others. Stamens united in an asymmetrical tube surrounding and covering the ovary. (a) Anthers: Hooded, colorless, infused heavily with red. (b) Pollen color: Cream. (2) Pistils: (a) Stigma: Five-pointed star, colorless. (b) Styles: Cream colored, very short. (c) Ovaries: 5, celled, size 5 mm., green in color.

Disease resistance: No general plant diseases noted. Insect problems can include the two-spotted spider mite which can cause foliar injury and thrips which can cause stunting and injury to the growing tip.

I claim:

1. A new and distinct cultivar of impatiens plant known by the cultivar name Vista Impatiens No. 60, as described and illustrated, and characterized by its very large, vivid dark salmon color flowers with a half eye, profuse blooming, dark green foliage, good self-branching habit, good keeping qualities, and tall, upright, and spreading form, making the cultivar suitable for bedding plants, hanging baskets and container culture.

* * * * *